US00PP21306P2

(12) United States Plant Patent
Danziger

(10) Patent No.: US PP21,306 P2
(45) Date of Patent: Sep. 21, 2010

(54) **NEW GUINEA *IMPATIENS* PLANT NAMED 'DANHAR305'**

(50) Latin Name: *Impatiens hawkeri*
Varietal Denomination: DANHAR305

(76) Inventor: Gabriel Danziger, PO Box 24, Moshav Mishmar Hashiva, Beit Dagan (IL) 50297

( * ) Notice: Subject to any disclaimer, the term of this patent is extended or adjusted under 35 U.S.C. 154(b) by 0 days.

(21) Appl. No.: 12/454,553

(22) Filed: May 18, 2009

(51) Int. Cl.
*A01H 5/00* (2006.01)

(52) U.S. Cl. ..... Plt./318.1

(58) Field of Classification Search ..... Plt./318.1, Plt./318.3
See application file for complete search history.

*Primary Examiner*—June Hwu

(57) ABSTRACT

A new and distinct *Impatiens* cultivar named 'DANHAR305' is disclosed, characterized by having a compact plant habit, free branching and distinct orange flowers with a white center. The new variety is an *Impatiens*, normally produced as an outdoor garden or container plant.

2 Drawing Sheets

Figure 1:
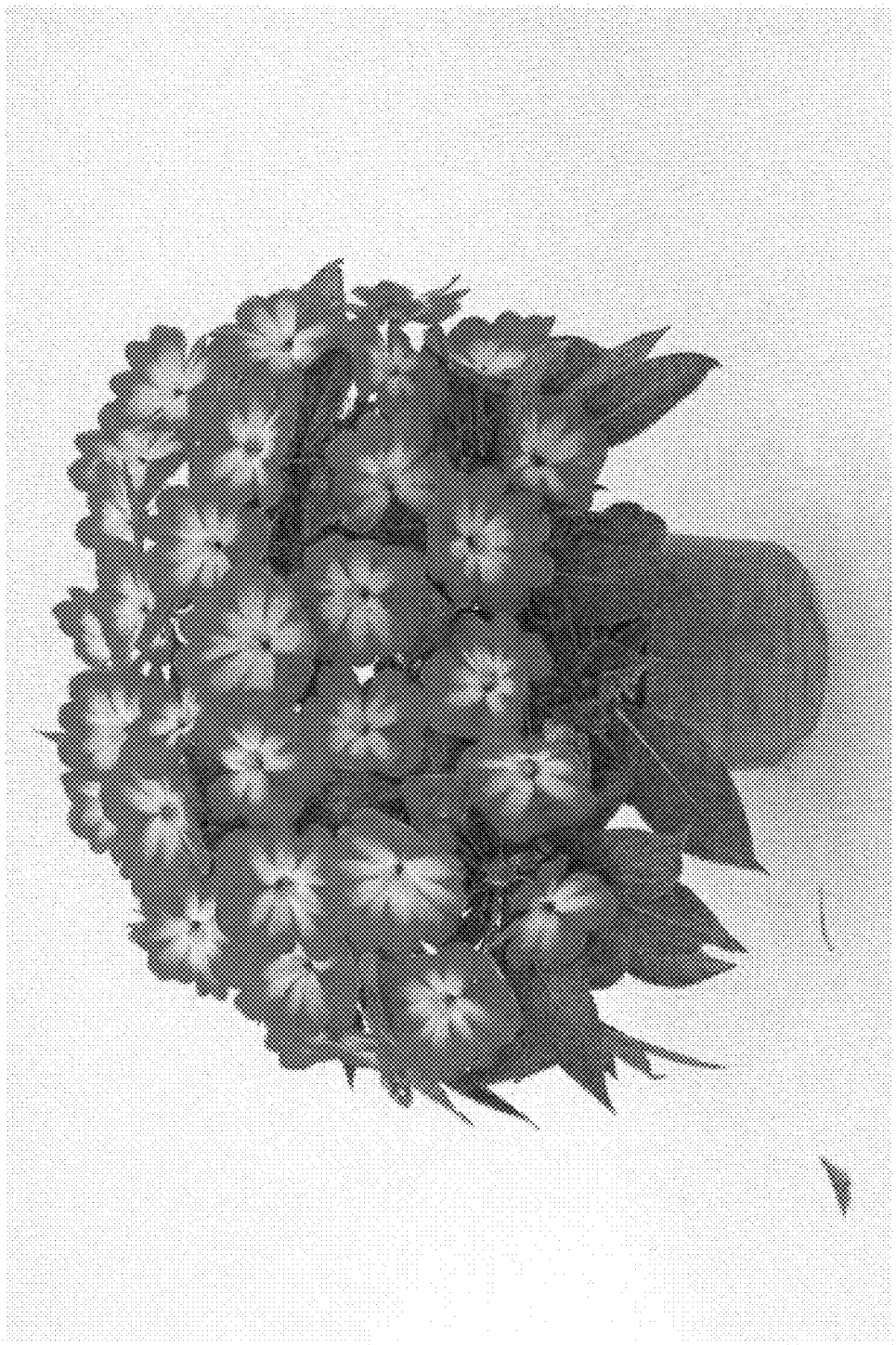

Latin name of the genus and species: *Impatiens hawkeri.*
Variety denomination: 'DANHAR305 '.

BACKGROUND OF THE INVENTION

The new *Impatiens* cultivar is a product of a planned breeding program conducted by the inventor, Gabriel Danziger, in Moshav Mishmar Hashiva, Israel. The objective of the breeding program was to produce new varieties of *Impatiens* for commercial introduction. The crossing resulting in the new cultivar was made in January 2006. The seed parent is the unpatented, proprietary seedling variety referred to as *Impatiens hawkeri* 'NGT-5-403.' The pollen parent is the unpatented, proprietary seedling variety referred to as *Impatiens hawkeri* 'NGT-5-776.' The new variety was discovered in July 2006 by the inventor in a group of seedlings resulting from that crossing, in a commercial greenhouse in Moshav Mishmar Hashiva, Israel.

Asexual reproduction of the new cultivar 'DANHAR305' by vegetative cuttings was first performed at a commercial greenhouse in Moshav Mishmar Hashiva, Israel in July 2006. Subsequent propagation has shown that the unique features of this cultivar are stable and reproduced true to type on successive generations.

SUMMARY OF THE INVENTION

The cultivar 'DANHAR305' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DANHAR305.' These characteristics in combination distinguish 'DANHAR305' as a new and distinct *Impatiens* cultivar:

1. Orange colored flowers .
2. Unique large white center of flower.

3. Free branching.
4. Compact growth habit.

PARENTAL COMPARISON

Plants of the new cultivar 'DANHAR305' are similar to plants of the seed parent, 'NGT-5-403' in most horticultural characteristics, however, plants of the new cultivar 'DANHAR305' have a more compact plant habit and earlier flowering. Additionally, the new variety produces flowers with a distinctive white eye, compared to a solid orange flower of the seed parent variety.

Plants of the new cultivar 'DANHAR305' are similar to plants of the pollen parent, 'NGT-5-776' in most horticultural characteristics, however, plants of the new cultivar 'DANHAR305' have a more compact plant habit, smaller flowers and flower earlier.

COMMERCIAL COMPARISON

Plants of the new cultivar 'DANHAR305' can be compared to the commercial variety 'DANHARCREAM,' unpatented in the United States. Plants of 'DANHAR305' are similar to plants of 'DANHARCREAM', in most horticultural characteristics, however, plants of the new cultivar 'DANHAR305' have a darker color flower, a less vigorous growth habit and lighter colored leaves.

Plants of the new cultivar 'DANHAR305' can be compared to the commercial variety 'DANHAR276,' unpatented in the United States. Plants of 'DANHAR305' are similar to plants of 'DANHAR276' in most horticultural characteristics, however, plants of the new cultivar 'DANHAR305' have flower petals in a lighter color, and different color pattern, a less vigorous growth habit and lighter colored leaves.

BRIEF DESCRIPTION OF THE PHOTOGRAPH

The accompanying photographs in FIG. 1 illustrates in full color a typical plant of 'DANHAR305' grown in a greenhouse, in a 12 cm pot.

Figure 2:
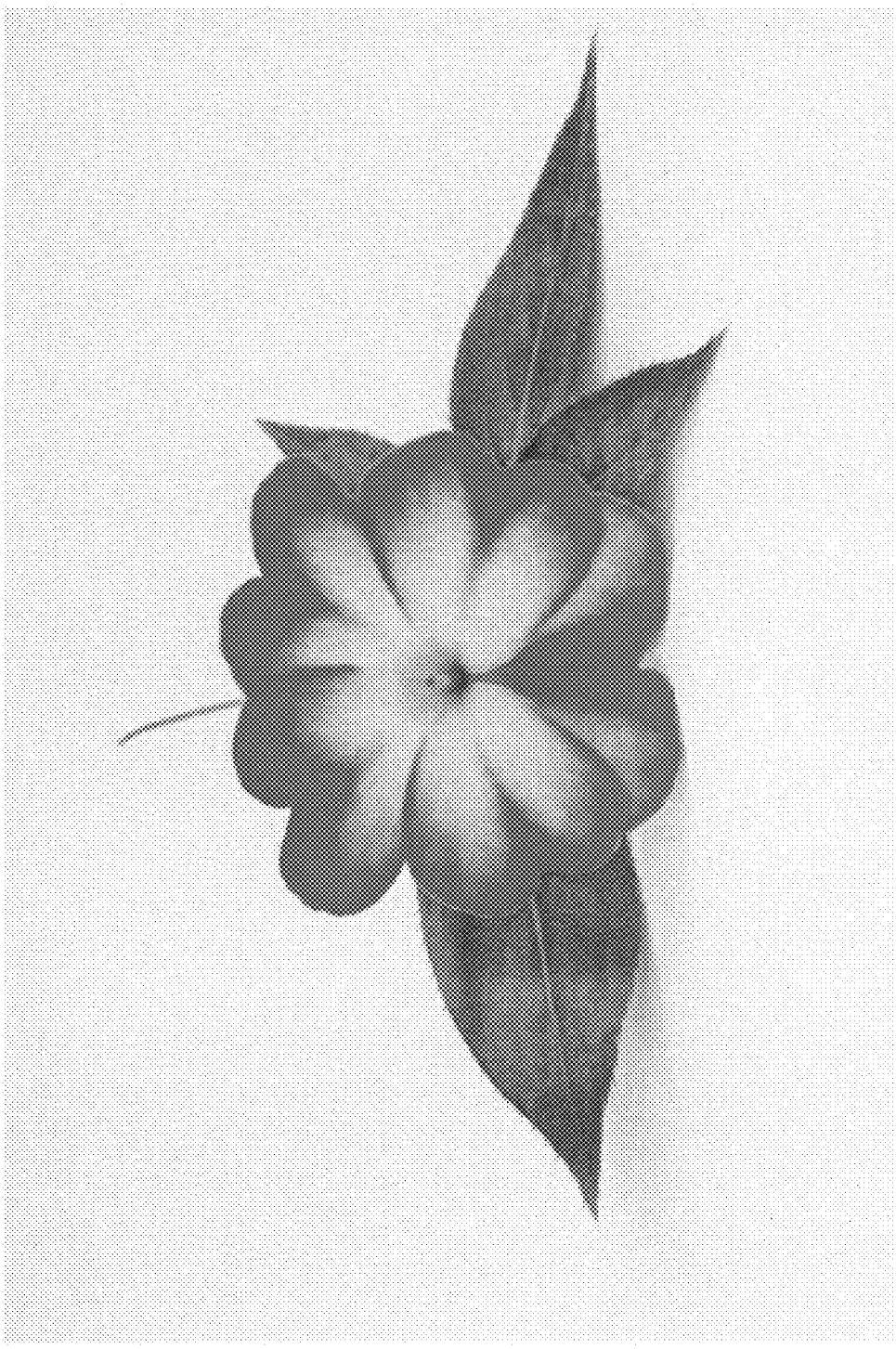

FIG. 2 illustrates in full color a typical flower of 'DANHAR305.' Age of the plant photographed is approximately 12 weeks from a rooted cutting, with 1 rooted cutting planted in the pot shown. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'DANHAR305' plants grown in a greenhouse in Moshav Mishmar Hashiva, Israel. The growing temperature ranged from day temperatures of 20° C. to 30° C., and night temperatures of 15° C. to 20° C. The greenhouse is unshaded, giving bright, normal sunlight conditions. No growth regulators or artificial light treatments were given. Measurements and numerical values represent averages of typical plant types.

Botanical classification: *Impatiens hawkeri* cultivar 'DANHAR305'.

PROPAGATION

Time to initiate roots: Summer: About 7 to 10 days at approximately 25° C. Winter: About 10 to 14 days at approximately 20° C.

Root description: Fibrous.

PLANT

Growth habit: Round and compact, very good branching.

Pot size of plant described: 12 cm.

Age of plant described: Approximately 12 weeks from a rooted cutting.

Height: Approximately 13 cm.

Plant spread: Approximately 30 cm.

Growth rate: Moderate.

Branching characteristics: Highly branched.

Length of primary lateral branches: Approximately 10 cm.

Quantity of primary lateral branches: Average 8.

Characteristics of primary lateral branches:

*Diameter.*—Approximately 0.8 cm.

*Color.*—Near RHS Yellow Green 146D.

*Texture.*—Smooth.

*Strength.*—Strong, resists breaking.

Internode length: Approximately 3 to 4 cm.

FOLIAGE

Leaf:

*Arrangement.*—Alternate.

*Quantity.*—Approximately 15-20 per branch.

*Average length.*—Approximately 9.0 cm.

*Average width.*—Approximately 3.5 cm.

*Shape of blade.*—Lanceolate to ovate.

*Apex.*—Attenuate.

*Margin.*—Crenate.

*Texture of top surface.*—Smooth.

*Pubescence.—none.*

*Aspect.*—45 degrees.

*Color.*—Young foliage upper side: Near RHS Green 137A. Young foliage under side: Near RHS Green Group 138B. Mature foliage upper side: Near RHS Green Group 137A. Mature foliage under side: Near RHS Green 138D.

*Venation.*—Upper surface: Pinnate. Strong midrib with secondary veins. Lower surface: Pinnate. Venation color upper side: Near RHS Yellow Green 149D. Venation color under side: Near RHS Yellow Green 147D.

*Petiole.*—Length: Approximately 1.5 cm. Diameter: Approximately 0.2 cm. Color: Near RHS Yellow Green 147D. Texture: Smooth.

FLOWER

Natural flowering season: Flowers at any day length. All year round in a greenhouse environment. Flowering is continuous from spring until fall in an outdoor garden.

Days to flowering from rooted cutting: Approximately 10 weeks.

Inflorescence and flower type and habit: Single flowers raised above the foliage. The corolla consists of five petals.

Rate of flower opening: 10 to 15 days from bud to fully opened flower.

Flower longevity on plant: 5-7 days.

Persistent or self-cleaning: Self-Cleaning.

Bud:

*Shape.*—Ovate.

*Length.*—Approximately 1.5 cm.

*Diameter.*—Approximately 1.0 cm.

*Color.*—Near RHS Orange Red Group 34D.

Flower size:

*Diameter.*—Approximately 6.5 cm.

*Depth.*—Approximately 0.3 cm.

Petals:

*Quantity.*—5.

*Arrangement.*—Overlapping.

*Length.*—Approximately 3.5 cm.

*Width.*—Approximately 4 cm.

*Shape.*—Round.

*Apex.*—Heart shape.

*Base.*—Acute.

*Margin.*—Entire.

*Texture, upper and lower surfaces.*—Smooth.

*Color.*—Orange. When opening, upper surface: Near RHS Orange Red 32A with White N155B. When opening, lower surface: Near RHS Red 40D. Fully opened, upper surface: Near RHS Red Group 32A with White N155B. Fully opened, lower surface: Near RHS Red 44D with Red Group 41D.

Spurs:

*Quantity per flower.*—1.

*Length.*—6 cm.

*Diameter.*—0.1 cm.

*Aspect.*—Spur curvature 40°-45° from peduncle.

*Color.*—Towards base: Near RHS Orange Red 35D. Apex: Near Yellow Green 147D.

Sepals:

*Quantity.*—2.

*Length.*—1.5 cm.

*Width.*—0.5 cm.

*Shape (overall).*—Oblong. Apex: Acute. Base: Rounded.

*Margin.*—Entire.

*Color.*—Near RHS Yellow Green 145C.

Peduncles:
*Length.*—Approximately 6 cm.
*Diameter.*—0.1 cm.
*Angle.*—About 45° to the lateral branch.
*Strength.*—Strong, flexible.
*Texture.*—Smooth.
*Color.*—Near RHS Yellow Green 145A.
Fragrance: None.

REPRODUCTIVE ORGANS

Stamens: There are five stamens with introrse anthers that are more or less fused and form a cap over the ovary.
*Number.*—5.
Anthers:
*Shape.*—Oblong.
*Length.*—Approximately 0.3 cm.
*Color.*—Near RHS white 155D.
*Pollen.*—Color: Near RHS White N155B. Quantity: Profuse.
Pistil:
*Number.*—1.
*Length.*—0.5 cm.
*Style.*—Length: 0.4 cm. Color: Near RHS Yellow Green 146C.
*Stigma.*—Shape: Round. Color: Near RHS Green-yellow group 1D. Ovary Color: Near RHS Yellow-Green 144D.

OTHER CHARACTERISTICS

Seeds and fruits: 10 to 20 seeds per fruit.
*Seed.*—Length: 2 mm. Diameter: 2 mm. Shape: Ovate. Texture: Puberulous. Color: Near RHS Greyed-Orange 17A.
*Fruit.*—Shape: Elliptic. Color: Near RHS Green 143C.
Disease/pest resistance: Neither resistance nor susceptibility to normal diseases and pests of *Impatiens* have been observed.
Temperature tolerance: The new variety tolerates temperatures between 10 to 30° C.

What is claimed is:

1. A new and distinct cultivar of *Impatiens* plant named 'DANHAR305' as herein illustrated and described.

* * * * *